US 12,133,815 B2

(12) United States Patent
Shulman et al.

(10) Patent No.: US 12,133,815 B2
(45) Date of Patent: Nov. 5, 2024

(54) EYE DROP APPLICATOR

(71) Applicant: Magic Touch Eye, Inc., New York, NY (US)

(72) Inventors: Julius Shulman, New York, NY (US); Tyler Panian, Naperville, IL (US); Emily Ruth Moyer, Brooklyn, NY (US)

(73) Assignee: Magic Touch Eye, Inc., New York, NY (US)

( * ) Notice: Subject to any disclaimer, the term of this patent is extended or adjusted under 35 U.S.C. 154(b) by 0 days.

(21) Appl. No.: 18/064,721

(22) Filed: Dec. 12, 2022

(65) Prior Publication Data

US 2023/0190524 A1 Jun. 22, 2023
US 2024/0033125 A9 Feb. 1, 2024

Related U.S. Application Data

(60) Provisional application No. 63/292,520, filed on Dec. 22, 2021.

(51) Int. Cl.
*A61F 9/00* (2006.01)
(52) U.S. Cl.
CPC .................. *A61F 9/0026* (2013.01)
(58) Field of Classification Search
CPC ...... A61F 9/0026; A61F 9/0008; A61H 35/02
See application file for complete search history.

(56) References Cited

U.S. PATENT DOCUMENTS

| 2,754,821 | A | * | 7/1956 | Burbig | A61H 35/02 604/301 |
|---|---|---|---|---|---|
| 5,373,964 | A | * | 12/1994 | Moore | A61F 9/0008 422/918 |
| 6,129,248 | A | * | 10/2000 | Hagele | A61F 9/0008 222/571 |
| 6,197,008 | B1 | * | 3/2001 | Hagele | B65D 47/18 604/295 |
| 6,632,202 | B1 | * | 10/2003 | Hagele | A61F 9/0008 604/295 |
| 7,165,701 | B2 | * | 1/2007 | Hirota | B65D 47/18 222/421 |
| 2004/0111070 | A1 | * | 6/2004 | Hanley | A61F 9/0008 604/295 |
| 2007/0113841 | A1 | * | 5/2007 | Fuchs | B05B 11/048 128/200.14 |
| 2007/0262096 | A1 | * | 11/2007 | Gaynes | A61F 9/0008 222/420 |

(Continued)

*Primary Examiner* — Sarah Al Hashimi
*Assistant Examiner* — Arjuna P Chatrathi
(74) *Attorney, Agent, or Firm* — Kilpatrick Townsend & Stockton LLP (57) ABSTRACT

An eye drop applicator includes an applicator body with a top cavity, a bottom cavity, and a dispensing channel connecting the bottom cavity with the top cavity such that a fluid can selectively flow through the dispensing channel to the top cavity. The top cavity includes an opening at a top end of the applicator body, and the bottom cavity includes a bottom opening at a bottom end of the applicator body. The bottom cavity may receive a portion of an applicator container within the bottom cavity to assemble the eye drop applicator with the applicator container containing the fluid to be dispensed.

11 Claims, 7 Drawing Sheets

(56) References Cited

U.S. PATENT DOCUMENTS

2013/0096517 A1* 4/2013 Leistner .................. B65B 3/006
  604/301
2017/0056241 A1* 3/2017 Shulman ............. A61M 35/003
2021/0389166 A1* 12/2021 Valavala ................ B65D 41/26

* cited by examiner

EYE DROP APPLICATOR

REFERENCE TO RELATED APPLICATION

This application claims the benefit of U.S. Provisional Patent Application No. 63/292,520, filed on Dec. 22, 2021 and entitled EYE DROP APPLICATOR, the content of which is hereby incorporated by reference in its entirety.

FIELD OF THE INVENTION

This application relates to systems and methods for applying eye drops.

BACKGROUND

Prescription and non-prescription eye drops are a common treatment for a variety of eye conditions. Conventional eye drop application techniques are often unsuccessful in applying just one drop into the conjunctival sac without wasted and expensive drops rolling down the face of the user.

SUMMARY

Embodiments covered by this patent are defined by the claims below, not this summary. This summary is a high-level overview of various embodiments and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

According to certain embodiments, an eye drop applicator includes an applicator body, and the applicator body includes a top cavity, a bottom cavity, and a dispensing channel connecting the bottom cavity with the top cavity. The top cavity includes an opening at a top end of the applicator body, and the bottom cavity includes a bottom opening at a bottom end of the applicator body. In some embodiments, the bottom cavity may receive a portion of an applicator container within the bottom cavity. The dispensing channel connects the bottom cavity with the top cavity such that a fluid can selectively flow through the dispensing channel and to the top cavity.

According to some embodiments, an eye drop applicator includes an applicator body with a top cavity, a bottom cavity, and a dispensing channel connecting the bottom cavity and the top cavity. In certain embodiments, the bottom cavity may receive a portion of an applicator container within the bottom cavity. The eye drop applicator also includes a flow controller at least partially within the top cavity, and the flow controller may control a flow of a fluid from the dispensing channel into the top cavity.

According to various embodiments, an eye drop applicator includes an applicator body with a top end, a bottom end, and an outer surface extending from the top end to the bottom end. The applicator body also includes a top cavity with an opening at the top end, a bottom cavity with a bottom opening at the bottom end, and a dispensing channel connecting the bottom cavity with the top cavity. In certain embodiments, a relief passage extends from the bottom cavity to the outer surface between the top end and the bottom end.

According to certain embodiments, an eye drop applicator includes an applicator body with a top cavity, a bottom cavity, and a dispensing channel connecting the bottom cavity with the top cavity. The top cavity includes an opening at a top end of the applicator body, and a bottom cavity includes a bottom opening at a bottom end of the applicator body. In some embodiments, the applicator body includes a tube engagement feature within the bottom cavity opposite from the bottom end. The tube engagement feature may at least partially define the dispensing channel and may selectively engage a dispensing tube within the bottom cavity.

According to some embodiments, an eye drop applicator includes an applicator body with a top cavity having an opening at a top end of the applicator body, a bottom cavity having a bottom opening at a bottom end of the applicator body, a dispensing channel connecting the bottom cavity with the top cavity, and a relief passage extending through the applicator body between the top end and the bottom end. The eye drop applicator also includes a relief controller for selectively opening and closing the relief passage.

Various implementations described herein may include additional systems, methods, features, and advantages, which cannot necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The specification makes reference to the following appended figures, in which use of like reference numerals in different figures is intended to illustrate like or analogous components.

DETAILED DESCRIPTION

Described herein are eye drop applicators that facilitate the measurement and administration of a liquid or fluid including, but not limited to, eye drops and/or other medication. In certain embodiments, the eye drop applicators are attachable to an applicator container such as an eye drop bottle holding a quantity of the fluid to be dispensed to facilitate measurement and administration of the fluid from the applicator container. The eye drop applicators may include various mating or engagement features such that a single eye drop applicator can be used with a plurality of applicator containers as desired. In some embodiments, the eye drop applicators described herein include flow controllers such that a predetermined quantity (or droplet) of the fluid is dispensed. In various embodiments, the eye drop applicators may include a relief passage that is selectively opened or closed by a relief controller to facilitate equalizing pressure within the eye drop applicator while minimizing potential siphoning of the droplet of the fluid back into the applicator container. Various other advantages may be realized with the eye drop applicators described herein, and the aforementioned advantages and benefits should not be considered limiting.

FIGS. 1-7 illustrate an example of an applicator assembly 100 according to various embodiments. As illustrated, the applicator assembly 100 generally includes an eye drop applicator 102 and an applicator container 104.

Figure 1:
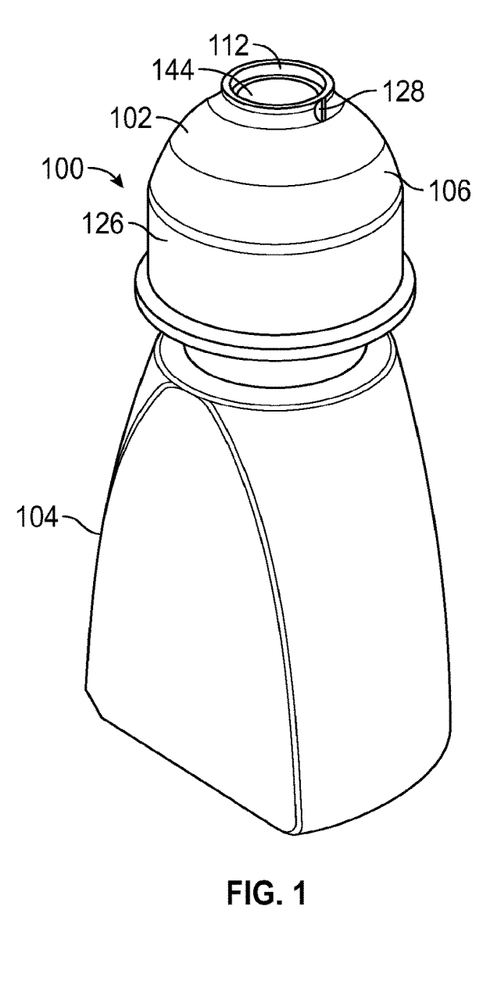
FIG. 1 is a perspective view of an applicator assembly according to embodiments.
Figure 2:
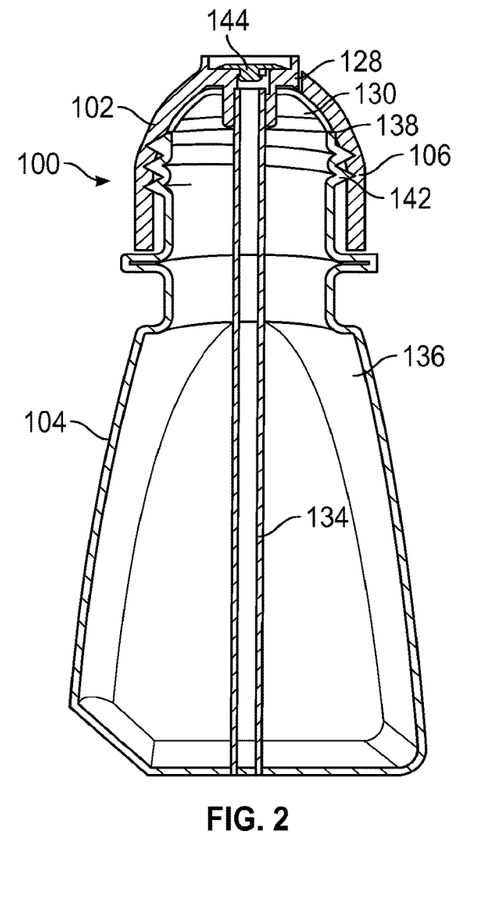
FIG. 2 is a sectional view of the applicator assembly of FIG. 1.

The applicator container 104 generally defines a chamber 136 for receiving a quantity of a fluid to be dispensed by the applicator assembly 100. A top end 138 of the applicator container 104 may define an opening 140 providing access to the chamber 136. Optionally, engagement features 142 are provided proximate to the opening 140 for selectively engaging the eye drop applicator 102 as discussed in detail below. In the embodiment illustrated, the engagement features 142 are threads; however, in other embodiments, other engagement features 142 may be utilized as desired to facilitate selective engagement between the eye drop applicator 102 and the applicator container 104, including but not limited to, adhesives, ribs, snap-fit connections, magnets, hooks, clips, combinations thereof, and/or various other features or mechanisms as desired.

In the embodiment illustrated, the applicator container 104 is an eye drop bottle and is constructed from a soft material (e.g., such as but not limited to polypropylene) such that it is compressible by a user to dispense a fluid from the chamber 136. In certain embodiments, the applicator container 104 may have a shape or profile to facilitate squeezing or compression by a user to provide improved metering of the fluid from the chamber 136. In one non-limiting example, the applicator container 104 may have an oblong shape such as an oval-shaped bottle or the bottle illustrated in FIGS. 1 and 2. However, the applicator container 104 may have various shapes, profiles, sizes, etc. as desired and may be constructed from various materials as desired, and the particular applicator container 104 illustrated should not be considered limiting.

Figure 3:
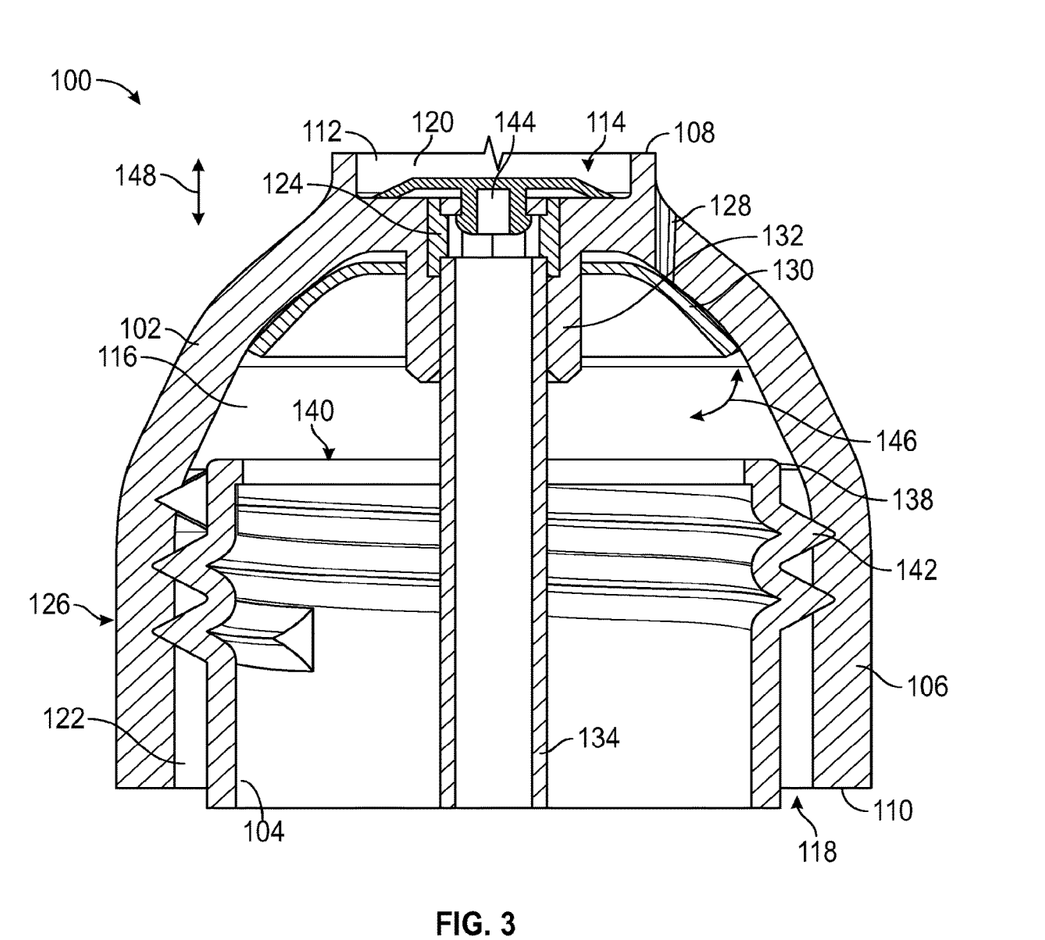
FIG. 3 is a sectional view of a portion of the applicator assembly of FIG. 1.
Figure 4:
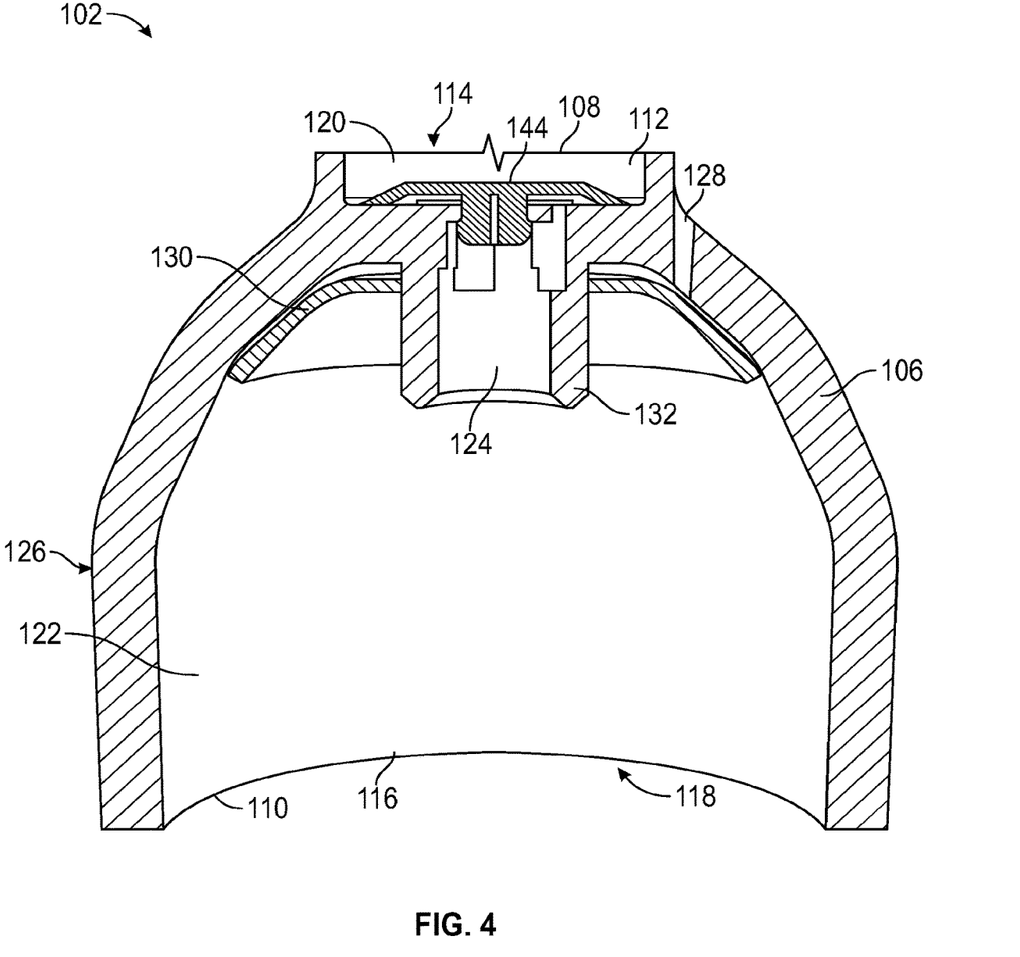
FIG. 4 is a sectional view of an eye drop applicator of the applicator assembly of FIG. 1.
Figure 5:
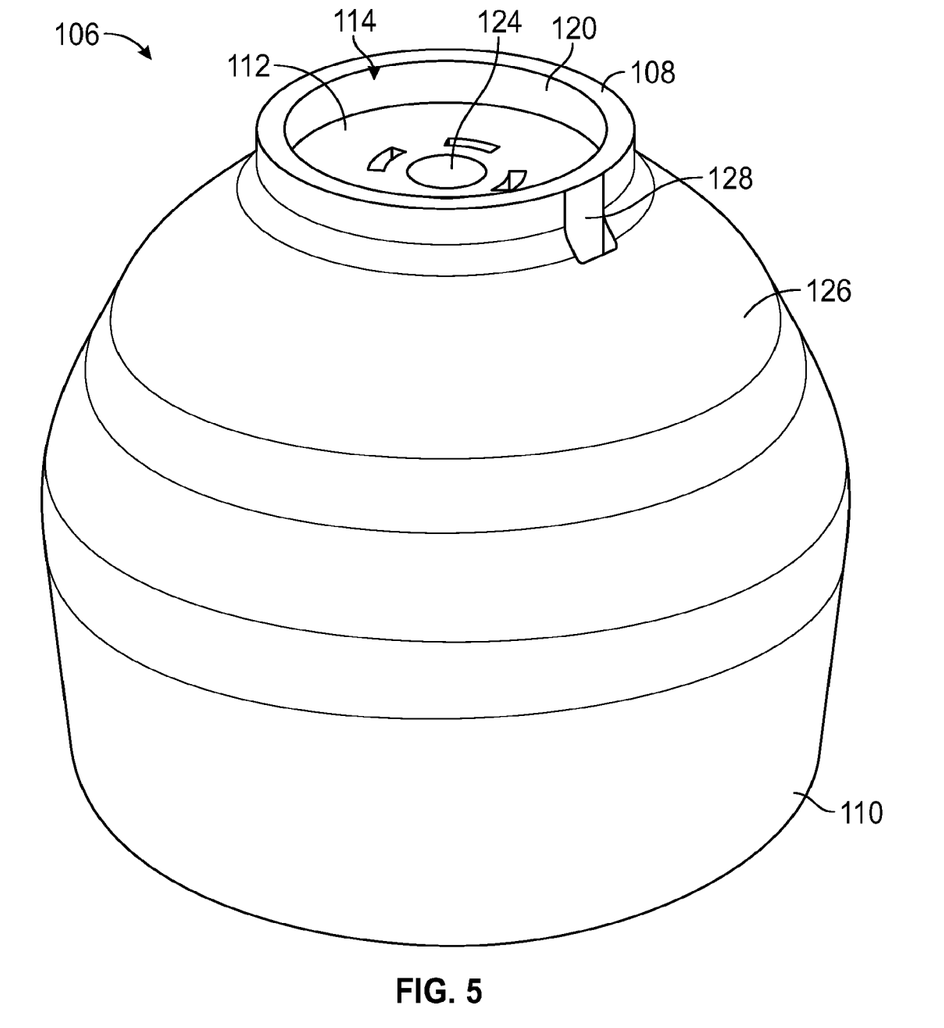
FIG. 5 illustrates a body of the eye drop applicator of FIG. 4 according to embodiments.

In certain embodiments, and as best illustrated in FIGS. 3-5, the eye drop applicator 102 includes an applicator body 106 having a top end 108, a bottom end 110 opposite from the top end 108, and an outer surface 126 extending from the top end 108 to the bottom end 110. The applicator body 106 may be constructed from various materials as desired. As some non-limiting examples, the applicator body 106 may be constructed from materials including, but not limited to, medical-grade silicone, rigid plastic, soft plastic, polycarbonate, polyethylene, polyethylene terephthalate, acrylonitrile butadiene styrene, and/or other similar materials.

As illustrated in FIGS. 3-5, for example, the applicator body 106 includes a top cavity 112 with an opening 114 in the top end 108 of the applicator body 106 and a bottom cavity 116 with an opening 118 in the bottom end 110 of the applicator body 106. The applicator body 106 also includes a dispensing channel 124 extending from the top cavity 112 to the bottom cavity 116.

The top cavity 112 includes a shape or profile for receiving a predetermined amount of a fluid from the applicator container 104 via the dispensing channel 124. In some embodiments, the predetermined amount may be 1-5 drops of fluid, such as 1-2 drops of fluid, such as about 1 drop of fluid; however, in other embodiments, the top cavity 112 may be sized to receive any desired amount of the fluid as desired. In the embodiment illustrated, the top cavity 112 includes a cavity surface 120 of which a portion of the cavity surface 120 is flat or planar; however, in other embodiments, the top cavity 112 may have other shapes or profiles as desired, and the particular cavity surface 120 illustrated should not be considered limiting.

Figure 6:
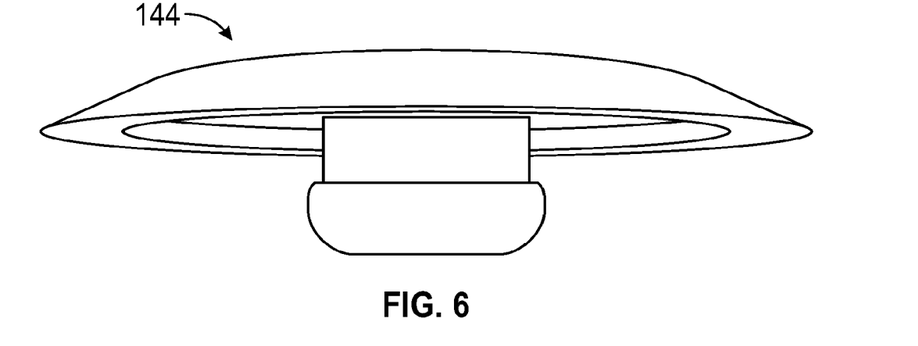
FIG. 6 illustrates a flow controller of the applicator of FIG. 4 according to embodiments.
Figure 7:
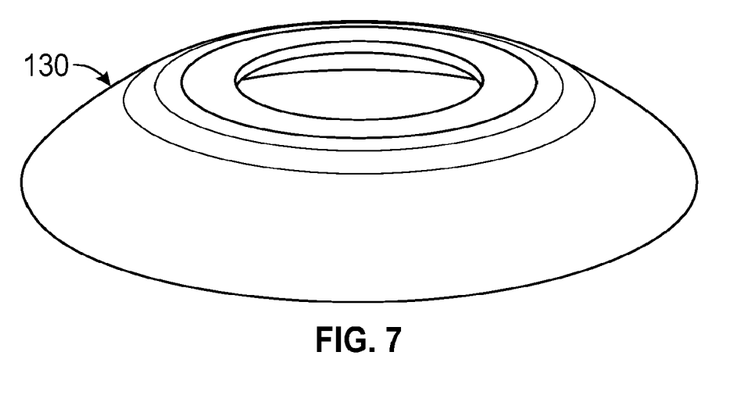
FIG. 7 illustrates a relief controller of the applicator of FIG. 4 according to embodiments.

As illustrated in FIGS. 3 and 4, for example, a flow controller 144 may be positioned at least partially within the dispensing channel 124 and/or the top cavity 112 for controlling the flow of fluid from the dispensing channel 124 into the top cavity 112. In certain embodiments, the flow controller 144 may enable flow through or otherwise open the dispensing channel 124 responsive to a pressurizing event (e.g., when the user squeezes the applicator container 104) and may obstruct flow through or otherwise close the dispensing channel 124 responsive to a vacuum event (e.g., when the user is no longer squeezing the applicator container 104 and the applicator assembly 100 is equalizing pressure). In various embodiments, such control from the flow controller 144 may allow for a controlled amount of fluid to be dispensed into the top cavity 112 without siphoning the fluid back into the applicator container 104, which may be important for safety reasons. In the embodiment illustrated, and as best illustrated in FIG. 6, the flow controller 144 is an umbrella valve. In this embodiment, the umbrella valve is movable relative to the applicator body 106 for controlling the flow of the fluid from the dispensing channel 124 and into the top cavity 112. Movement of the flow controller 144 between an open position and a closed position relative to the dispensing channel 124 in this embodiment is represented by arrow 148 in FIG. 3. However, other types of flow controllers 144 may be utilized as desired, and the particular positioning and/or type of flow controller 144 should not be considered limiting.

The bottom cavity 116 includes a cavity surface 122 and has a shape or profile suitable for receiving at least a portion of the applicator container 104 within the bottom cavity 116 such as the top end 138 of the applicator container 104 as illustrated in FIG. 2. In some embodiments, at least one characteristic of the bottom cavity 116 (e.g., volume, shape, size, profile, etc.) is different from the top cavity 112. In certain embodiments, the cavity surface 122 optionally includes one or more engagement features suitable for engaging the portion of the applicator container 104 and/or the engagement features 142 of the applicator container 104. As some non-limiting examples, the cavity surface 122 may include an adhesive coating, threads, snap-fit connectors, ribs, grooves, combinations thereof, and/or other engagement features as desired for selectively engaging the applicator container 104 and such that the eye drop applicator 102 is repeatedly attachable to and detachable from the applicator container 104 as desired. In other embodiments, specific engagement features need not be included on the cavity surface 122. As a non-limiting example, the applicator body 106 may be constructed from a pliable or deformable material such that the cavity surface 122 selectively deforms to engage the applicator container 104. Optionally, sealing members (not illustrated) may be provided to further seal the interface between the applicator container 104 and the applicator body 106 for improved performance and control. Such sealing members may be various devices or mechanisms as desired, such as but not limited to rubber or elastomer gaskets and/or rings, ribs on the applicator container 104 and/or the applicator body 106, and/or other suitable materials or combinations of materials as desired. In other embodiments, sealing members need not be provided.

Optionally, and as best illustrated in FIGS. 3 and 4, the applicator body 106 includes a tube engagement feature 132 extending from the cavity surface 122 and into the bottom cavity 116. In certain embodiments, when the tube engagement features 132 is included, it may at least partially define the dispensing channel 124. As illustrated in FIGS. 2 and 3, a dispensing tube 134 of the applicator assembly 100 may engage with and/or be supported by the tube engagement feature 132. When included, the dispensing tube 134 defines a flow path for a fluid from the chamber 136 of the applicator container 104 and to the dispensing channel 124. In such embodiments, the dispensing tube 134 may be provided with the eye drop applicator 102 such that a desired amount of fluid may be dispensed from the applicator container 104 and through the dispensing channel 124 while the applicator assembly 100 is in a generally upright configuration (e.g., as illustrated in FIGS. 1 and 2). In other embodiments, the dispensing tube 134 may be omitted, and a flow path of fluid may be from the chamber 136, into the bottom cavity 116, through the dispensing channel 124, and into the top cavity 112.

In certain embodiments, and as best illustrated in FIGS. 3 and 4, the applicator body 106 includes a relief passage 128 that extends from the outer surface 126 to the cavity surface 122 of the bottom cavity 116. The particular location of the relief passage 128 should not be considered limiting, and in various embodiments, the relief passage 128 may be provided at any location as desired between the top end 108 and the bottom end 110 of the applicator body 106. In certain embodiments, the relief passage 128 allows a gas (e.g., air) to enter the bottom cavity 116, and when the eye drop applicator 102 is assembled with the applicator container 104, the relief passage 128 allows the gas to enter the applicator container 104.

In some embodiments, the eye drop applicator 102 includes a relief controller 130 for controlling the flow of gas through the relief passage 128. In some embodiments, the relief controller 130 may enable flow through or otherwise open the relief passage 128 during certain events (e.g., a vacuum event when the applicator body 104 is equalizing pressure within the chamber 136) and may obstruct flow through or otherwise close the relief passage 128 during other events (e.g., dispensing of fluid through the dispensing channel 124). In the embodiment illustrated, the relief controller 130 is a flexible disc supported on the tube engagement feature 132, and the flexible disc is constructed from silicone or other flexible material. Movement of the flexible disc of this embodiment between an open position and a closed position relative to the relief passage 128 is represented by arrow 146 in FIG. 3. However, the particular relief controller 130 illustrated should not be considered limiting. For example, in other embodiments, the relief controller 130 need not be a separate component, and instead a relief controller for controlling the relief passage 128 may be integrally or monolithically formed with the applicator body 106. Moreover, in other embodiments, the relief controller 130 may be constructed from materials other than silicone and/or may have other shapes or profiles other than the flexible disc shape illustrated.

Optionally, one or more surfaces of the applicator assembly 100 may be treated with an antimicrobial coating either during the manufacturing process or after the manufacturing process is complete. In some examples, the coating may include silver ions and/or particles of a thermoplastic polymer containing an organic biocide where the coating is electrostatically sprayed onto the one or more surfaces (or formed as part of the surfaces during the manufacturing process). In addition, the coating may be any known type of antimicrobial coating. When included, the coating may be applied to any surface or combinations of surfaces as desired including, but not limited to, the cavity surface 120 and the cavity surface 122.

Referring to FIGS. 1-3, a method of using the applicator assembly 100 will be described in detail. In certain embodiments, a user may squeeze or compress the applicator container 104 to increase pressure within the chamber 136. The increased pressure within the chamber 136 may cause the relief controller 130 to close the relief passage 128 and may cause the fluid within the chamber 136 to flow through the dispensing tube 134 and to the dispensing channel 124. The closing of the relief passage 128 by the relief controller 130 may create an enclosed volume which allows for the generation of internal pressure within the chamber 136. Optionally, the relief controller 130 may minimize or prevent the fluid from being dispensed through the relief passage 128. The increased pressure and/or fluid directed into the dispensing channel 124 may in turn cause the flow controller 144 to move to its open position such that the fluid can flow from the dispensing channel 124 into the top cavity 112.

In certain embodiments, when a desired amount of the fluid is directed into the top cavity 112, the user releases and/or otherwise stops applying pressure to the applicator container 104 to stop directing fluid through the dispensing channel 124. The removal of this force by the user creates a vacuum event within the chamber 136. In certain embodiments, the flow controller 144 may be "normally closed," meaning that it does not necessarily need any vacuum pressure to close. In such embodiments, the flow controller 144 may need a positive pressure (e.g., from squeezing of the applicator container or bottle) to open the flow controller 144.

The pressure from the vacuum event may also cause the relief controller 130 to move to its open position relative to the relief passage 128 such that gas can enter the chamber 136 and equalize the pressure within the chamber 136. The user may raise the applicator assembly 100 to the recipient's eye similar to a motion for inserting a contact lens such that a portion of the fluid within the top cavity 112 touches the eye. Such contact with the recipient's eye disrupts the surface tension of the fluid within the top cavity 112, and the fluid flows from the top cavity 112 to the recipient's eye via gravity and/or capillary action.

FIGS. 8-12 illustrate another example of an applicator assembly 800 according to various embodiments. Similar to the applicator assembly 100, the applicator assembly 800 generally includes an eye drop applicator 802 and the applicator container 104. In addition, similar to the applicator assembly 100, the applicator assembly 800 includes an applicator body 806, the dispensing tube 134 and the flow controller 144.

Figure 8:
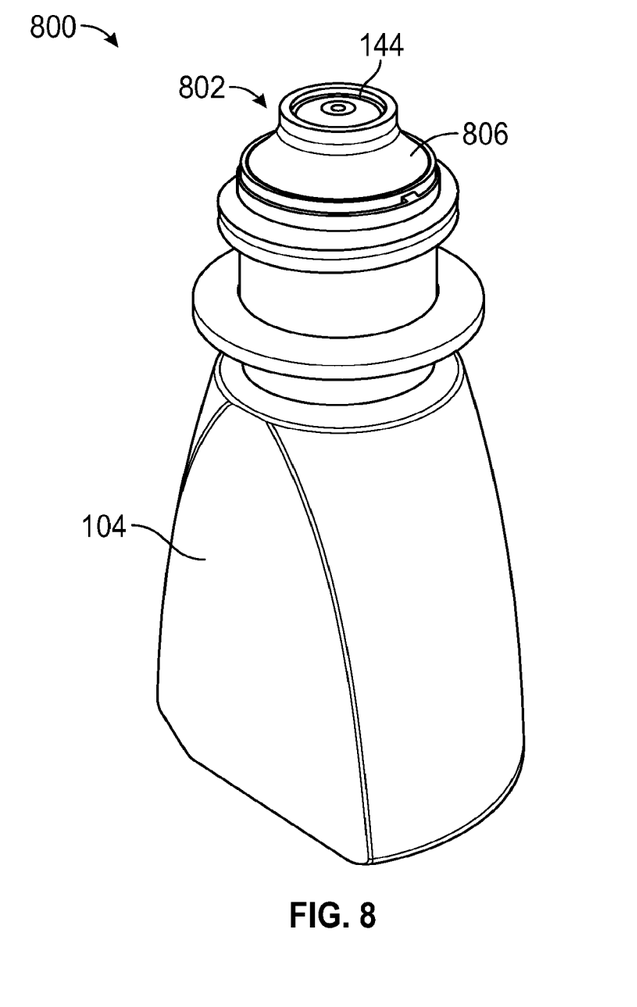
FIG. 8 is a perspective view of an applicator assembly according to embodiments.
Figure 9:
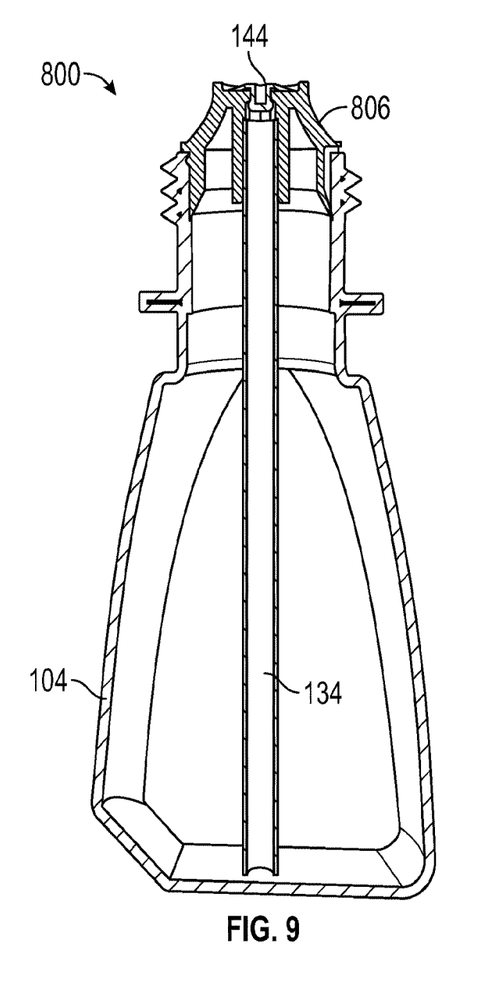
FIG. 9 is a sectional view of the applicator assembly of FIG. 8.
Figure 12:
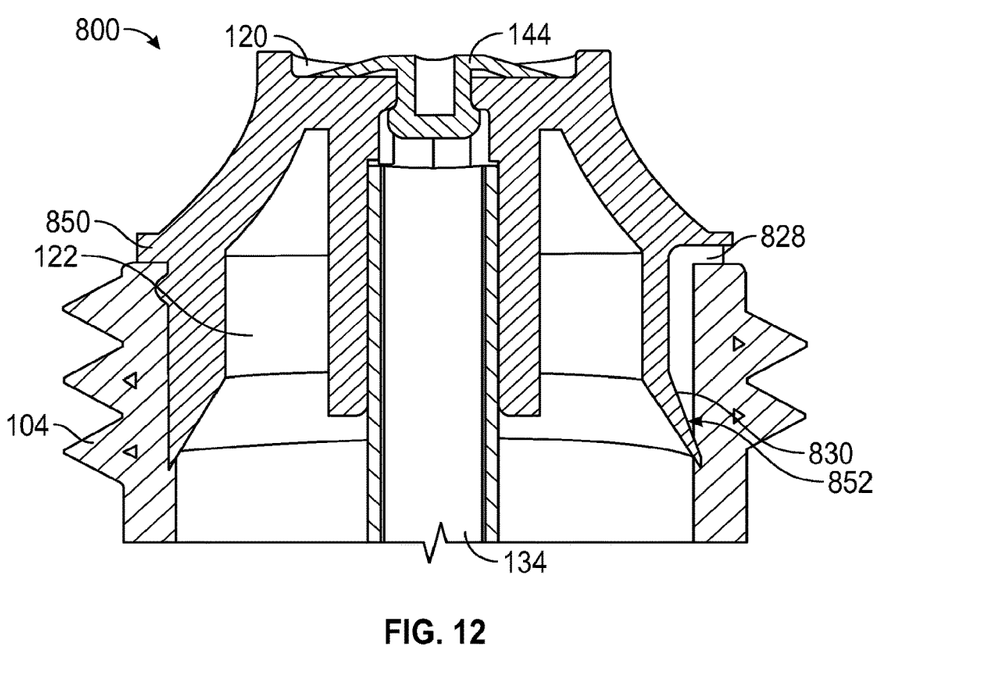
FIG. 12 is a sectional view of a portion of the applicator assembly of FIG. 8.

The applicator body 806 is substantially similar to the applicator body 106 except that the applicator body 806 includes a rib 850 extending outwards from the outer surface 126 of the applicator body 806. As best illustrated in FIGS. 8, 9, and 12, compared to the applicator body 106, which receives a portion of the applicator container 104 within the bottom cavity 116, at least a portion of an applicator body 806 is positioned within the opening 140 of the applicator container 104. Optionally, the rib 850 abuts the top end 138 of the applicator container 104. In such embodiments, the rib 850 abutting the top end 138 optionally may seal the applicator container 104. Optionally, a portion of the outer surface 126 of the applicator body 806 may additionally or alternatively contact the applicator container 104 within the chamber 136, and such contact may seal the applicator container 104.

Figure 10:
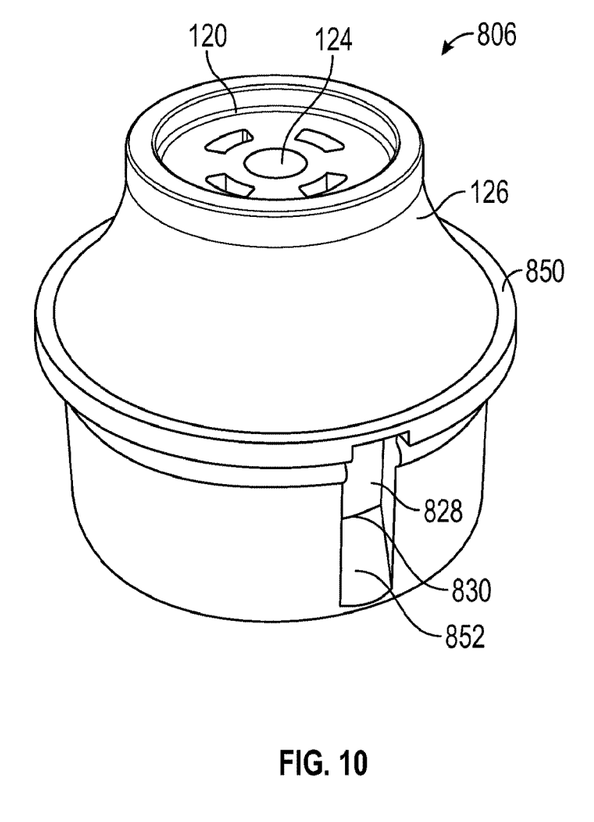
FIG. 10 is a perspective view of a body of an eye drop applicator of the applicator assembly of FIG. 8.
Figure 11:
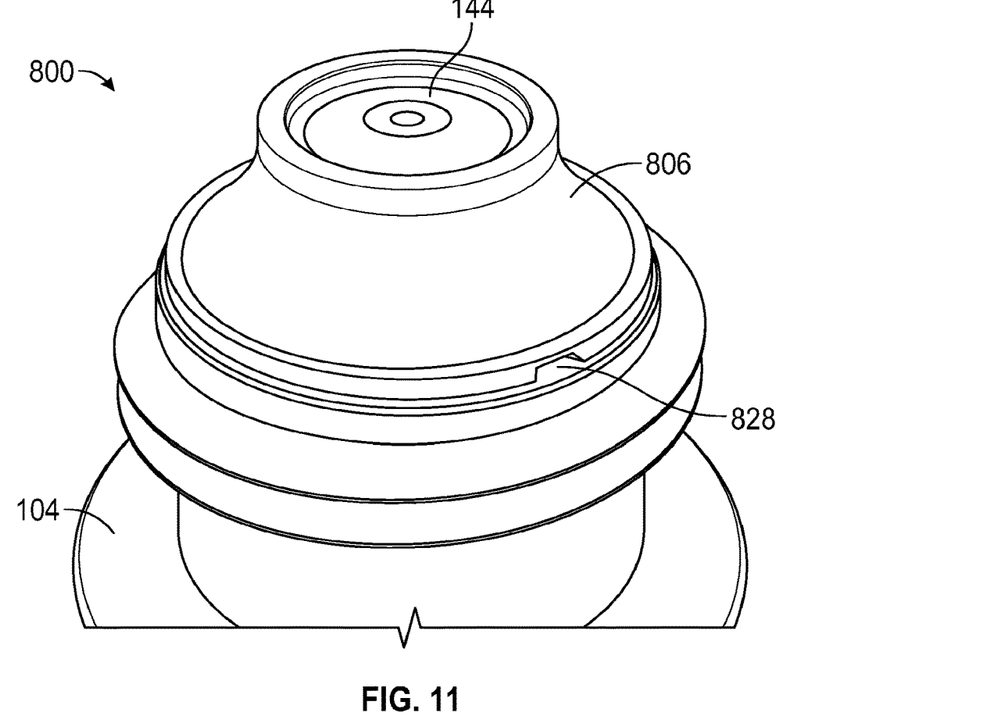
FIG. 11 is perspective view of a portion of the applicator assembly of FIG. 8.

As best illustrated in FIGS. 10-12, compared to the applicator body 106, the applicator body 806 also includes a relief controller 830 integrally or monolithically formed with the applicator body 806. In this embodiment, the a relief passage 828 is a channel or groove in the applicator body 806, and the relief controller 830 is a channel or groove surface 852 that selectively interfaces with the inside of the applicator container 104 to control the flow of gas through the relief passage 828.

A collection of exemplary embodiments are provided below, including at least some explicitly enumerated as "Illustrations" providing additional description of a variety of example embodiments in accordance with the concepts described herein. These illustrations are not meant to be mutually exclusive, exhaustive, or restrictive; and the disclosure not limited to these example illustrations but rather encompasses all possible modifications and variations within the scope of the issued claims and their equivalents.

Illustration 1. An eye drop applicator comprising an applicator body, the applicator body comprising: a top cavity comprising an opening at a top end of the applicator body; a bottom cavity comprising a bottom opening at a bottom end of the applicator body, wherein the bottom cavity is configured to receive a portion of an applicator container within the bottom cavity; and a dispensing channel connecting the bottom cavity with the top cavity such that a fluid can selectively flow through the dispensing channel and to the top cavity.

Illustration 2. The eye drop applicator of any preceding or subsequent illustrations or combination of illustrations, wherein a volume of the top cavity is less than a volume of the bottom cavity, and wherein the top cavity is configured to retain a predetermined amount of a liquid medication as the fluid.

Illustration 3. The eye drop applicator of any preceding or subsequent illustrations or combination of illustrations, wherein the applicator body further comprises a container engagement feature within the bottom cavity for selectively engaging the portion of the applicator container within the bottom cavity.

Illustration 4. The eye drop applicator of any preceding or subsequent illustrations or combination of illustrations, wherein the applicator body comprises silicone.

Illustration 5. The eye drop applicator of any preceding or subsequent illustrations or combination of illustrations, further comprising the applicator container, and wherein the applicator container is compressible.

Illustration 6. An eye drop applicator comprising: an applicator body comprising a top cavity, a bottom cavity, and a dispensing channel connecting the bottom cavity and the top cavity, wherein the bottom cavity is configured to receive a portion of an applicator container within the bottom cavity; and a flow controller at least partially within the top cavity, wherein the flow controller is configured to control a flow of a fluid from the dispensing channel into the top cavity.

Illustration 7. The eye drop applicator of any preceding or subsequent illustrations or combination of illustrations, wherein the flow controller comprises a valve, wherein the valve is at least partially within the dispensing channel.

Illustration 8. The eye drop applicator of any preceding or subsequent illustrations or combination of illustrations, wherein the flow controller is movable relative to the applicator body.

Illustration 9. An eye drop applicator comprising an applicator body, the applicator body comprising: a top end; a bottom end; an outer surface extending from the top end to the bottom end; a top cavity comprising an opening at the top end; a bottom cavity comprising a bottom opening at the bottom end; a dispensing channel connecting the bottom cavity with the top cavity; and a relief passage extending from the bottom cavity to the outer surface between the top end and the bottom end.

Illustration 10. The eye drop applicator of any preceding or subsequent illustrations or combination of illustrations, further comprising a relief controller configured to selectively open and close the relief passage.

Illustration 11. The eye drop applicator of any preceding or subsequent illustrations or combination of illustrations, further comprising a flow controller configured to control a flow of fluid from the dispensing channel to the top cavity.

Illustration 12. The eye drop applicator of any preceding or subsequent illustrations or combination of illustrations, further comprising: a tube engagement feature within the bottom cavity opposite from the bottom end, wherein the tube engagement feature at least partially defines the dispensing channel; and a dispensing tube engaged with the tube engagement feature within the bottom cavity and such that the dispensing tube is in fluid communication with the dispensing channel.

Illustration 13. An eye drop applicator comprising an applicator body, the applicator body comprising: a top cavity comprising an opening at a top end of the applicator body; a bottom cavity comprising a bottom opening at a bottom end of the applicator body; a dispensing channel connecting the bottom cavity with the top cavity; and a tube engagement feature within the bottom cavity opposite from the bottom end, wherein the tube engagement feature at least partially defines the dispensing channel and is configured to selectively engage a dispensing tube within the bottom cavity.

Illustration 14. The eye drop applicator of any preceding or subsequent illustrations or combination of illustrations, further comprising the dispensing tube engaged with the tube engagement feature and such that the dispensing tube is in fluid communication with the dispensing channel.

Illustration 15. The eye drop applicator of any preceding or subsequent illustrations or combination of illustrations, further comprising: a flow controller at least partially within the top cavity, wherein the flow controller is configured to control a flow of a fluid from the dispensing channel into the top cavity.

Illustration 16. The eye drop applicator of any preceding or subsequent illustrations or combination of illustrations, wherein the applicator body further comprises a relief passage defined in the applicator body and extending from the bottom cavity to an outer surface of the applicator body between the top end and the bottom end.

Illustration 17. The eye drop applicator of any preceding or subsequent illustrations or combination of illustrations, further comprising a relief controller configured to selectively open and close the relief passage.

Illustration 18. An eye drop applicator comprising: an applicator body, the applicator body comprising: a top cavity comprising an opening at a top end of the applicator body; a bottom cavity comprising a bottom opening at a bottom end of the applicator body; a dispensing channel connecting the bottom cavity with the top cavity; and a relief passage extending through the applicator body between the top end and the bottom end; and a relief controller configured to selectively open and close the relief passage.

Illustration 19. The eye drop applicator of any preceding or subsequent illustrations or combination of illustrations, wherein the relief controller is monolithically formed with the applicator body.

Illustration 20. The eye drop applicator of any preceding or subsequent illustrations or combination of illustrations, wherein the applicator body further comprises a tube engagement feature within the bottom cavity opposite from the bottom end, wherein the tube engagement feature at least partially defines the dispensing channel and is configured to selectively engage a dispensing tube within the bottom cavity, and wherein the relief controller is supported on the tube engagement feature.

The subject matter of embodiments is described herein with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described. Directional references such as "up," "down," "top," "bottom," "left," "right," "front," and "back," among others, are intended to refer to the orientation as illustrated and described in the figure (or figures) to which the components and directions are referencing. In the figures and the description, like numerals are intended to represent like elements. While the embodiments provided herein are described in the context of eye drops, in other embodiments, the applicator may be used for various other application techniques and/or with other fluids as desired.

The above-described aspects are merely possible examples of implementations, merely set forth for a clear understanding of the principles of the present disclosure. Many variations and modifications may be made to the above-described embodiment(s) without departing substantially from the spirit and principles of the present disclosure. All such modifications and variations are intended to be included herein within the scope of the present disclosure, and all possible claims to individual aspects or combinations of elements or steps are intended to be supported by the present disclosure. Moreover, although specific terms are employed herein, as well as in the claims that follow, they are used only in a generic and descriptive sense, and not for the purposes of limiting the described embodiments, nor the claims that follow.

That which is claimed:

1. An eye drop applicator comprising:
    an applicator body comprising a top cavity, a bottom cavity, and a dispensing channel connecting the bottom cavity and the top cavity, wherein the bottom cavity is configured to receive a portion of an applicator container within the bottom cavity; and
    a flow controller at least partially within the top cavity, wherein the flow controller is configured to control a flow of a fluid from the dispensing channel into the top cavity.

2. The eye drop applicator of claim 1, wherein the flow controller comprises a valve, wherein the valve is at least partially within the dispensing channel.

3. The eye drop applicator of claim 1, wherein the flow controller is movable relative to the applicator body.

4. An eye drop applicator comprising an applicator body, the applicator body comprising:
    a top end;
    a bottom end;
    an outer surface extending from the top end to the bottom end;
    a top cavity comprising an opening at the top end;
    a bottom cavity comprising a bottom opening at the bottom end;
    a dispensing channel connecting the bottom cavity with the top cavity; and
    a relief passage extending through the applicator body from the bottom cavity to the outer surface and opening into the bottom cavity at a location more proximate to the top end than the bottom end.

5. The eye drop applicator of claim 4, further comprising a relief controller configured to selectively open and close the relief passage.

6. The eye drop applicator of claim 4, further comprising a flow controller configured to control a flow of fluid from the dispensing channel to the top cavity.

7. The eye drop applicator of claim 4, further comprising:
    a tube engagement feature within the bottom cavity opposite from the bottom end, wherein the tube engagement feature at least partially defines the dispensing channel; and
    a dispensing tube engaged with the tube engagement feature within the bottom cavity and such that the dispensing tube is in fluid communication with the dispensing channel.

8. An eye drop applicator comprising an applicator body, the applicator body comprising:
    a top cavity comprising an opening at a top end of the applicator body;
    a bottom cavity comprising a bottom opening at a bottom end of the applicator body;
    a dispensing channel connecting the bottom cavity with the top cavity;
    a flow controller at least partially within the top cavity, wherein the flow controller is configured to control a flow of a fluid from the dispensing channel into the top cavity; and
    a tube engagement feature within the bottom cavity opposite from the bottom end, wherein the tube engagement feature at least partially defines the dispensing channel and is configured to selectively engage a dispensing tube within the bottom cavity.

9. The eye drop applicator of claim 8, further comprising the dispensing tube engaged with the tube engagement feature and such that the dispensing tube is in fluid communication with the dispensing channel.

10. The eye drop applicator of claim 8, wherein the applicator body further comprises a relief passage defined in the applicator body and extending from the bottom cavity to an outer surface of the applicator body between the top end and the bottom end.

11. The eye drop applicator of claim 10, further comprising a relief controller configured to selectively open and close the relief passage.

* * * * *